United States Patent
Zhou et al.

(10) Patent No.: US 12,031,165 B2
(45) Date of Patent: Jul. 9, 2024

(54) DOUBLE ENZYME TANDEM PREPARATION METHOD OF L-2-AMINOBUTYRIC ACID

(71) Applicant: Jiangnan University, Wuxi (CN)

(72) Inventors: Zhemin Zhou, Wuxi (CN); Zhongmei Liu, Wuxi (CN); Yufeng Liu, Wuxi (CN); Li Zhou, Wuxi (CN); Wenjing Cui, Wuxi (CN); Junling Guo, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 525 days.

(21) Appl. No.: 17/477,668

(22) Filed: Sep. 17, 2021

(65) Prior Publication Data

US 2021/0403895 A1 Dec. 30, 2021

Related U.S. Application Data

(63) Continuation of application No. PCT/CN2020/131276, filed on Nov. 25, 2020.

(30) Foreign Application Priority Data

Jan. 18, 2020 (CN) .......................... 202010058267.1

(51) Int. Cl.
*C12P 13/04* (2006.01)
*C12N 9/88* (2006.01)
*C12N 9/90* (2006.01)

(52) U.S. Cl.
CPC ................ *C12N 9/88* (2013.01); *C12N 9/90* (2013.01); *C12P 13/04* (2013.01); *C12Y 401/01012* (2013.01); *C12Y 504/03009* (2015.07)

(58) Field of Classification Search
CPC .. C12N 9/88; C12N 9/90; C12N 15/70; C12P 13/04; C12Y 401/01012; C12Y 504/03009
See application file for complete search history.

(56) References Cited

U.S. PATENT DOCUMENTS

2011/0166335 A1* 7/2011 Corbin .................. C07K 14/24
536/23.5

FOREIGN PATENT DOCUMENTS

| CN | 105671098 A | 6/2016 |
|----|-------------|--------|
| CN | 106148259 A | 11/2016 |

(Continued)

OTHER PUBLICATIONS

Xu et al., Fermentative production of the unnatural amino acid l-2-aminobutyric acid based on metabolic engineering, 2019, Microb Cell Fact18:43 (Year: 2019).*

(Continued)

*Primary Examiner* — Soren Harward
*Assistant Examiner* — Naghmeh Nina Moazzami
(74) *Attorney, Agent, or Firm* — IPRO, PLLC

(57) ABSTRACT

Disclosed is a double enzyme tandem preparation method of L-2-aminobutyric acid, and belongs to the field of bioengineering. In the disclosure, recombinant *Escherichia coli* expressing L-glutamate mutase and recombinant *Escherichia coli* expressing L-aspartate-β-decarboxylase are separately cultured to obtain L-glutamate mutase and L-aspartate-β-decarboxylase. The two enzymes are added to a reaction system at a certain mass ratio, and L-glutamate is used as a substrate to carry out an enzyme reaction to (Continued)

prepare the L-2-aminobutyric acid. When the dosage of the L-aspartate-β-decarboxylase is 2 mg/mL, and the reaction time is 24 h, 8.5 mmol/L L-2-aminobutyric acid is produced by conversion, with a molar conversion rate of 85.00%. Compared with a chemical production method, the method disclosed by the disclosure has a safe production process and no environmental pollution. Compared with a multi-enzyme synthesis system with threonine as a substrate, the substrate is cheaper and the process is simpler.

12 Claims, 1 Drawing Sheet

Specification includes a Sequence Listing.

(56) References Cited

FOREIGN PATENT DOCUMENTS

| | | |
|---|---|---|
| CN | 109266595 A | 1/2019 |
| CN | 109536429 A | 3/2019 |
| CN | 109777845 A | 5/2019 |
| CN | 111172213 A | 5/2020 |

OTHER PUBLICATIONS

Zhu et al., Removal of L-alanine from the production of L-2-aminobutyric acid by introduction of alanine racemase and D-amino acid oxidase, 2011, Biotechnological Products and Process Engineering, vol. 90, p. 903-910. (Year: 2011).*

Liu Y.F. et al., "Enzymatic Biosynthesis of L-2-Aminobutyric Acid by Glutamate Mutase Coupled with L-Aspartate-—decarboxylase Using L-Glutamate as the Sole Substrate", ACS Catalysis, vol. 10, Iss. 23, Nov. 16, 2020, 1-13p. 13913-13917.

Chen H.P. et al., "Adenosylcobalamin-Dependent Glutamate Mutase: Examination of Substrate and Coenzyme Binding in an Engineered Fusion Protein Possessing Simplified Subunit Structure and Kinetic Properties", Biochemistry, vol. 36 No. 48, Dec. 31, 1997, 1-13, p. 14939-14945.

Pan Gousheng et. al. "Advance in the biosynthesis of L-2-aminobutyrate" Fermentation Technology Newsletter vol. 45 No. 3, Aug. 31, 2016, p. 182-187.

Liu shan et. al., "One-pot Enzymatic Synthesis of L-2-Aminobutyric Acid Coupling witha NADH egeneration System Based on Ketoreductase" China Biotechnology Dec. 31, 2017 37(1) : 64-70.

* cited by examiner

SEQUENCE LISTING

```
<160> NUMBER OF SEQ ID NOS: 9

<210> SEQ ID NO 1
<211> LENGTH: 533
<212> TYPE: PRT
<213> ORGANISM: Artificial sequence
<220> FEATURE:
<223> OTHER INFORMATION: Protein translated from synthetic DNA

<400> SEQUENCE: 1

Met Gly Asn Val Asp Tyr Ser Lys Tyr Ser Lys Leu Ser Pro Phe Glu
1               5                   10                  15

Leu Ala Asp Ser Leu Ile Ala Leu Ala Gln Ser Lys Arg Asp Arg Leu
            20                  25                  30

Met Leu Asn Ala Gly Arg Gly Asn Pro Asn Phe Leu Ala Thr Leu Pro
        35                  40                  45

Arg Arg Ala Phe Phe Gln Leu Gly Leu Phe Ser Ala Thr Glu Ser Glu
    50                  55                  60

Phe Ser Phe Ser Tyr Met Pro Glu Gly Leu Gly Gly Phe Pro Arg Pro
65                  70                  75                  80

Val Gly Leu Gln Ser Arg Phe Asp Asn Phe Leu Met Gln Asn Arg Asp
                85                  90                  95

Lys Pro Gly Val Leu Phe Leu Gly Lys Ala Val Ser Tyr Val Arg Asp
            100                 105                 110

Gln Leu Gly Leu Asp Pro Asp Met Phe Leu Leu Glu Met Val Glu Gly
        115                 120                 125

Ile Leu Gly Cys Asn Tyr Pro Val Pro Asp Arg Met Leu Arg Val Ser
    130                 135                 140

Glu Thr Ile Ile Lys Glu Tyr Leu Leu Gln Glu Met Gly Val Lys Ser
145                 150                 155                 160

Met Pro Lys Glu Gly Leu Asp Leu Phe Ala Val Glu Gly Gly Thr Ala
                165                 170                 175

Ala Met Ala Tyr Ile Phe Asn Ser Leu Lys Glu Asn Lys Ile Ile Asn
            180                 185                 190

Thr Asp Asp Arg Ile Ala Ile Gly Arg Pro Ile Phe Thr Pro Tyr Leu
        195                 200                 205

Glu Ile Pro Lys Leu Asn Asp Tyr Gln Leu Glu Ile Phe Ile Glu
    210                 215                 220

Ala Asp Pro Asn Leu Gly Trp Gln Tyr Pro Glu Ser Glu Leu Arg Lys
225                 230                 235                 240

Leu Glu Asp Pro Ser Ile Lys Ala Phe Phe Leu Val Asn Pro Ser Asn
                245                 250                 255

Pro Pro Ser Val Lys Ile Ser Asp Glu Gly Leu Leu Ile Leu Ala Asp
            260                 265                 270

Ile Val Arg Lys Arg Pro Asp Leu Ile Ile Leu Thr Asp Asp Ile Tyr
        275                 280                 285

Gly Thr Phe Ala Asp Asp Phe Lys Ser Leu Phe Ala Ile Cys Pro Asn
```

```
                290                 295                 300
Asn Thr Ile Leu Val Tyr Ser Phe Ser Lys Tyr Phe Gly Ala Thr Gly
305                 310                 315                 320

Trp Arg Leu Gly Ile Ile Ala Leu Ser Asn Asn Ile Ile Asp Gln
                325                 330                 335

Lys Ile Ala Ala Leu Ser Asp Gln Glu Lys Gln Leu Glu Glu Arg
                340                 345                 350

Tyr Ser Ser Leu Thr Thr Glu Pro Glu Lys Ile Lys Phe Ile Asp Arg
                355                 360                 365

Leu Val Ala Asp Ser Arg Asn Val Ala Leu Asn His Thr Ala Gly Leu
                370                 375                 380

Ser Thr Pro Gln Gln Val Gln Met Val Leu Phe Ala Leu Phe Asn Met
385                 390                 395                 400

Met Asp Ser Arg Gln Ala Tyr Lys Lys Ala Val Lys Ser Val Val Arg
                405                 410                 415

Glu Arg Asp Ala Ala Leu Tyr Arg Gln Leu Gly Val Glu Val Pro Glu
                420                 425                 430

Asp Leu Asn Ala Val Asp Tyr Tyr Thr Leu Val Asp Leu Glu Arg Thr
                435                 440                 445

Ala Arg Ile Leu Tyr Gly Asp Asp Phe Ala Asn Trp Val Met Val Asn
                450                 455                 460

Lys Asn Pro Thr Glu Leu Leu Phe Arg Val Ala Asp Glu Thr Gly Val
465                 470                 475                 480

Val Leu Leu Pro Gly Ser Gly Phe Gly Val Ser His Pro Ser Ala Arg
                485                 490                 495

Ala Ser Leu Ala Asn Leu Asn Ala Tyr Gln Tyr Ala Ala Ile Gly Asp
                500                 505                 510

Ser Leu Arg Arg Phe Ala Glu Asp Ala Tyr Gln Glu Tyr Leu Gly Thr
                515                 520                 525

Lys Lys Asp Glu Ser
                530

<210> SEQ ID NO 2
<211> LENGTH: 533
<212> TYPE: PRT
<213> ORGANISM: Artificial sequence
<220> FEATURE:
<223> OTHER INFORMATION: Protein translated from synthetic DNA

<400> SEQUENCE: 2

Met Gly Asn Val Asp Tyr Ser Tyr Ser Lys Leu Ser Pro Phe Glu
1               5                   10                  15

Leu Ala Asp Ser Leu Ile Ala Leu Ala Gln Ser Lys Arg Asp Arg Leu
                20                  25                  30

Met Leu Asn Ala Gly Arg Gly Asn Pro Asn Phe Leu Ala Thr Leu Pro
            35                  40                  45

Arg Arg Ala Phe Phe Gln Leu Gly Leu Phe Ser Ala Thr Glu Ser Glu
        50                  55                  60

Phe Ser Phe Ser Tyr Met Pro Glu Gly Leu Gly Phe Pro Arg Pro
65                  70                  75                  80

Val Gly Leu Gln Ser Arg Phe Asp Asn Phe Leu Met Gln Asn Arg Asp
                85                  90                  95

Lys Pro Gly Val Leu Phe Leu Gly Lys Ala Val Ser Tyr Val Arg Asp
                100                 105                 110

Gln Leu Gly Leu Asp Pro Asp Met Phe Leu Leu Glu Met Val Glu Gly
```

-continued

```
                115                 120                 125
Ile Leu Gly Cys Asn Tyr Pro Val Pro Asp Arg Met Leu Arg Val Ser
            130                 135                 140
Glu Thr Ile Ile Lys Glu Tyr Leu Leu Gln Glu Met Gly Val Lys Ser
145                 150                 155                 160
Met Pro Lys Glu Gly Leu Asp Leu Phe Ala Val Glu Gly Gly Thr Ala
                165                 170                 175
Ala Met Ala Tyr Ile Phe Asn Ser Leu Lys Glu Asn Lys Ile Ile Asn
                180                 185                 190
Thr Asp Asp Arg Ile Ala Ile Gly Arg Pro Ile Phe Thr Pro Tyr Leu
            195                 200                 205
Glu Ile Pro Lys Leu Asn Asp Tyr Gln Leu Glu Glu Ile Phe Ile Glu
210                 215                 220
Ala Asp Pro Asn Leu Gly Trp Gln Tyr Pro Ser Glu Leu Arg Lys
225                 230                 235                 240
Leu Glu Asp Pro Ser Ile Lys Ala Phe Phe Leu Val Asn Pro Ser Asn
                245                 250                 255
Pro Pro Ser Val Lys Ile Ser Asp Glu Gly Leu Leu Ile Leu Ala Asp
            260                 265                 270
Ile Val Arg Lys Arg Pro Asp Leu Ile Ile Leu Thr Asp Asp Leu Tyr
            275                 280                 285
Gly Thr Phe Ala Asp Asp Phe Lys Ser Leu Phe Ala Ile Cys Pro Asn
290                 295                 300
Asn Thr Ile Leu Val Tyr Ser Phe Ser Lys Tyr Phe Gly Ala Thr Gly
305                 310                 315                 320
Trp Arg Leu Gly Ile Ile Ala Leu Ser Asn Asn Ile Ile Asp Gln
                325                 330                 335
Lys Ile Ala Ala Leu Ser Asp Gln Glu Lys Gln Glu Leu Glu Glu Arg
            340                 345                 350
Tyr Ser Ser Leu Thr Thr Glu Pro Gly Lys Ile Lys Phe Ile Asp Arg
            355                 360                 365
Leu Val Ala Asp Ser Arg Asn Val Ala Leu Asn His Thr Ala Gly Leu
            370                 375                 380
Ser Thr Pro Gln Gln Val Gln Met Val Leu Phe Ala Leu Phe Asn Met
385                 390                 395                 400
Met Asp Ser Arg Gln Ala Tyr Lys Lys Ala Val Lys Ser Val Val Arg
                405                 410                 415
Glu Arg Asp Ala Ala Leu Tyr Arg Gln Leu Gly Val Glu Val Pro Glu
                420                 425                 430
Asp Leu Asn Ala Val Asp Tyr Tyr Thr Leu Val Asp Leu Glu Arg Thr
            435                 440                 445
Ala Arg Ile Leu Tyr Gly Asp Asp Phe Ala Asn Trp Val Met Val Asn
            450                 455                 460
Lys Asn Pro Thr Glu Leu Leu Phe Arg Val Ala Asp Glu Thr Gly Val
465                 470                 475                 480
Val Leu Leu Pro Gly Ser Gly Phe Gly Val Ser His Pro Ser Ala Arg
                485                 490                 495
Ala Ser Leu Ala Asn Leu Asn Ala Tyr Gln Tyr Ala Ala Ile Gly Asp
            500                 505                 510
Ser Leu Arg Arg Phe Ala Glu Asp Ala Tyr Gln Glu Tyr Leu Gly Thr
            515                 520                 525
Lys Lys Asp Glu Ser
            530
```

```
<210> SEQ ID NO 3
<211> LENGTH: 533
<212> TYPE: PRT
<213> ORGANISM: Artificial sequence
<220> FEATURE:
<223> OTHER INFORMATION: Protein translated from synthetic DNA

<400> SEQUENCE: 3

Met Gly Asn Val Asp Tyr Ser Lys Tyr Ser Lys Leu Ser Pro Phe Glu
1               5                   10                  15

Leu Ser Asp Ser Leu Ile Ala Leu Ala Gln Ser Lys Arg Asp Arg Leu
            20                  25                  30

Met Leu Asn Ala Gly Arg Gly Asn Pro Asn Phe Leu Ala Thr Leu Pro
        35                  40                  45

Arg Arg Ala Phe Phe Gln Leu Gly Leu Phe Ser Ala Thr Glu Ser Glu
    50                  55                  60

Phe Ser Phe Ser Tyr Met Pro Glu Gly Leu Gly Gly Phe Pro Arg Pro
65                  70                  75                  80

Val Gly Leu Gln Ser Arg Phe Asp Asn Phe Leu Met Gln Asn Arg Asp
                85                  90                  95

Lys Pro Gly Val Leu Phe Leu Gly Lys Ala Val Ser Tyr Val Arg Asp
            100                 105                 110

Gln Leu Gly Leu Asp Pro Asp Met Phe Leu Leu Glu Met Val Glu Gly
        115                 120                 125

Ile Leu Gly Cys Asn Tyr Pro Val Pro Asp Arg Met Leu Arg Val Ser
    130                 135                 140

Glu Thr Ile Ile Lys Glu Tyr Leu Leu Gln Glu Met Gly Val Lys Ser
145                 150                 155                 160

Met Pro Lys Glu Gly Leu Asp Leu Phe Ala Val Glu Gly Thr Ala
                165                 170                 175

Ala Met Ala Tyr Ile Phe Asn Ser Leu Lys Glu Asn Lys Ile Ile Asn
            180                 185                 190

Thr Asp Asp Arg Ile Ala Ile Gly Arg Pro Ile Phe Thr Pro Tyr Leu
        195                 200                 205

Glu Ile Pro Lys Leu Asn Asp Tyr Gln Leu Glu Glu Ile Phe Ile Glu
    210                 215                 220

Ala Asp Pro Asn Leu Gly Trp Gln Tyr Pro Glu Ser Glu Leu Arg Lys
225                 230                 235                 240

Leu Glu Asp Pro Ser Ile Lys Ala Phe Phe Leu Val Asn Pro Ser Asn
                245                 250                 255

Pro Pro Ser Val Lys Ile Ser Asp Glu Gly Leu Leu Ile Leu Ala Asp
            260                 265                 270

Ile Val Arg Lys Arg Pro Asp Leu Ile Ile Leu Thr Asp Asp Ile Tyr
        275                 280                 285

Gly Thr Phe Ala Asp Asp Phe Lys Ser Leu Phe Ala Ile Cys Pro Asn
    290                 295                 300

Asn Thr Ile Leu Val Tyr Ser Phe Ser Lys Tyr Phe Gly Ala Thr Gly
305                 310                 315                 320

Trp Arg Leu Gly Ile Ile Ala Leu Ser Asn Asn Asn Ile Ile Asp Gln
                325                 330                 335

Lys Ile Ala Ala Leu Ser Asp Gln Glu Lys Gln Glu Leu Glu Glu Arg
            340                 345                 350

Tyr Ser Ser Leu Thr Thr Glu Pro Glu Lys Ile Lys Phe Ile Asp Arg
        355                 360                 365
```

```
Leu Val Ala Asp Ser Arg Asn Val Ala Leu Asn His Thr Ala Gly Leu
            370                 375                 380

Ser Thr Pro Gln Gln Val Gln Met Val Leu Phe Ala Leu Phe Asn Met
385                 390                 395                 400

Met Asp Ser Arg Gln Ala Tyr Lys Lys Ala Val Lys Ser Val Val Arg
                405                 410                 415

Glu Arg Asp Ala Ala Leu Tyr Arg Gln Leu Gly Val Glu Val Pro Glu
            420                 425                 430

Asp Leu Asn Ala Val Asp Tyr Tyr Thr Leu Val Asp Leu Glu Arg Thr
            435                 440                 445

Ala Arg Ile Leu Tyr Gly Asp Asp Phe Ala Asn Trp Val Met Val Asn
            450                 455                 460

Lys Asn Pro Thr Glu Leu Leu Phe Arg Val Ala Asp Glu Thr Gly Val
465                 470                 475                 480

Val Leu Leu Pro Gly Ser Gly Phe Gly Val Ser His Pro Ser Ala Arg
                485                 490                 495

Ala Ser Leu Ala Asn Leu Asn Ala Tyr Gln Tyr Ala Ala Ile Gly Asp
                500                 505                 510

Ser Leu Arg Arg Phe Ala Glu Asp Ala Tyr Gln Glu Tyr Leu Gly Thr
            515                 520                 525

Lys Lys Asp Glu Ser
    530

<210> SEQ ID NO 4
<211> LENGTH: 533
<212> TYPE: PRT
<213> ORGANISM: Artificial sequence
<220> FEATURE:
<223> OTHER INFORMATION: Protein translated from synthetic DNA

<400> SEQUENCE: 4

Met Gly Asn Val Asp Tyr Ser Lys Tyr Ser Lys Leu Ser Pro Phe Glu
1               5                   10                  15

Leu Ser Asp Ser Leu Ile Ala Leu Ala Gln Ser Lys Arg Asp Arg Leu
                20                  25                  30

Met Leu Asn Ala Gly Arg Gly Asn Pro Asn Phe Leu Ala Thr Leu Pro
            35                  40                  45

Arg Arg Ala Phe Phe Gln Leu Gly Leu Phe Ser Ala Thr Glu Ser Glu
50                  55                  60

Phe Ser Phe Ser Tyr Met Pro Glu Gly Leu Gly Gly Phe Pro Arg Pro
65                  70                  75                  80

Val Gly Leu Gln Ser Arg Phe Asp Asn Phe Leu Met Gln Asn Arg Asp
                85                  90                  95

Lys Pro Gly Val Leu Phe Leu Gly Lys Ala Val Ser Tyr Val Arg Asp
            100                 105                 110

Gln Leu Gly Leu Asp Pro Asp Met Phe Leu Leu Glu Met Val Glu Gly
            115                 120                 125

Ile Leu Gly Cys Asn Tyr Pro Val Pro Asp Arg Met Leu Arg Val Ser
130                 135                 140

Glu Thr Ile Ile Lys Glu Tyr Leu Leu Gln Glu Met Gly Val Lys Ser
145                 150                 155                 160

Met Pro Lys Glu Gly Leu Asp Leu Phe Ala Val Glu Gly Gly Thr Ala
                165                 170                 175

Ala Met Ala Tyr Ile Phe Asn Ser Leu Lys Glu Asn Lys Ile Ile Asn
            180                 185                 190
```

Thr Asp Asp Arg Ile Ala Ile Gly Arg Pro Ile Phe Thr Pro Tyr Leu
          195                 200                 205

Glu Ile Pro Lys Leu Asn Asp Tyr Gln Leu Glu Glu Ile Phe Ile Glu
    210                 215                 220

Ala Asp Pro Asn Leu Gly Trp Gln Tyr Pro Glu Ser Glu Leu Arg Lys
225                 230                 235                 240

Leu Glu Asp Pro Ser Ile Lys Ala Phe Phe Leu Val Asn Pro Ser Asn
                245                 250                 255

Pro Pro Ser Val Lys Ile Ser Asp Glu Gly Leu Leu Ile Leu Ala Asp
                    260                 265                 270

Ile Val Arg Lys Arg Pro Asp Leu Ile Ile Leu Thr Asp Asp Leu Tyr
            275                 280                 285

Gly Thr Phe Ala Asp Asp Phe Lys Ser Leu Phe Ala Ile Cys Pro Asn
        290                 295                 300

Asn Thr Ile Leu Val Tyr Ser Phe Ser Lys Tyr Phe Gly Ala Thr Gly
305                 310                 315                 320

Trp Arg Leu Gly Ile Ile Ala Leu Ser Asn Asn Ile Ile Asp Gln
                325                 330                 335

Lys Ile Ala Ala Leu Ser Asp Gln Glu Lys Gln Glu Leu Glu Glu Arg
            340                 345                 350

Tyr Ser Ser Leu Thr Thr Glu Pro Glu Lys Ile Lys Phe Ile Asp Arg
        355                 360                 365

Leu Val Ala Asp Ser Arg Asn Val Ala Leu Asn His Thr Ala Gly Leu
    370                 375                 380

Ser Thr Pro Gln Gln Val Gln Met Val Leu Phe Ala Leu Phe Asn Met
385                 390                 395                 400

Met Asp Ser Arg Gln Ala Tyr Lys Lys Ala Val Lys Ser Val Val Arg
                405                 410                 415

Glu Arg Asp Ala Ala Leu Tyr Arg Gln Leu Gly Val Glu Val Pro Glu
                420                 425                 430

Asp Leu Asn Ala Val Asp Tyr Tyr Thr Leu Val Asp Leu Glu Arg Thr
            435                 440                 445

Ala Arg Ile Leu Tyr Gly Asp Asp Phe Ala Asn Trp Val Met Val Asn
        450                 455                 460

Lys Asn Pro Thr Glu Leu Leu Phe Arg Val Ala Asp Glu Thr Gly Val
465                 470                 475                 480

Val Leu Leu Pro Gly Ser Gly Phe Gly Val Ser His Pro Ser Ala Arg
                485                 490                 495

Ala Ser Leu Ala Asn Leu Asn Ala Tyr Gln Tyr Ala Ala Ile Gly Asp
                500                 505                 510

Ser Leu Arg Arg Phe Ala Glu Asp Ala Tyr Gln Glu Tyr Leu Gly Thr
            515                 520                 525

Lys Lys Asp Glu Ser
530

<210> SEQ ID NO 5
<211> LENGTH: 1893
<212> TYPE: DNA
<213> ORGANISM: Artificial sequence
<220> FEATURE:
<223> OTHER INFORMATION: Synthetic DNA

<400> SEQUENCE: 5
atggaactta aaataaaaa atggactgat gaagagtttc ataaacaaag agaaggta      60

-continued

| | |
|---|---|
| ctacaacaat ggccaactgg taaagaagta gatttacaag aggctgttga ttatttaaag | 120 |
| aaaataccag cagaaaagaa ttttgctgaa aaattagttt tagctaagaa aaaaggaata | 180 |
| actatggctc aaccaagagc tggagttgct ctattagatg aacatataga attattaaga | 240 |
| tatttacaag atgaaggtgg agcagacttt ttaccttcaa caattgatgc ttatacaaga | 300 |
| caaaatagat atgacgaatg tgaaaatggt ataaagaaa gtgaaaaagc aggaagatca | 360 |
| ttattaaatg gtttcccagg agttaattat ggtgttaagg gatgtagaaa agttttagaa | 420 |
| gcagttaact taccactaca agcaagacac ggtacaccag actcaagatt attagcagaa | 480 |
| ataattcacg caggtggatg gacttcaaat gaaggaggag gtatctccta caatgttcca | 540 |
| tatgcaaaga atgttacaat agaaaaaagc ttattagatt ggcaatattg tgatagactt | 600 |
| gttggtttct atgaagaaca aggtgttcat ataaacagag aaccatttgg tccattgaca | 660 |
| ggaacacttg taccaccatc aatgtcaaat gcagttggaa ttacagaagc attacttgca | 720 |
| gcagaacaag gtgttaagaa cataacagtt ggatacggtg aatgtggaaa catgatccaa | 780 |
| gatatagctg cattaagatg tctagaagaa caaacaaatg aatatttaaa agcttatgga | 840 |
| tataatgatg tatttgtaac tacagtattc caccaatgga tgggaggatt cccacaagat | 900 |
| gaatcaaagg catttggtgt tatagttaca gctactacta tagcagcttt agcaggagct | 960 |
| acaaaagtta tagttaagac tcctcatgaa gcaattggta taccaacaaa agaagcaaat | 1020 |
| gctgcaggaa taaagctac taagatggct ttaaatatgt tagaaggaca aagaatgcca | 1080 |
| atgtccaaag aattagaaac tgaaatggct gtaatcaagg ctgaaactaa atgtatcctt | 1140 |
| gacaaaatgt ttgaattagg aaagggagat ttagctatag gtacagttaa agcatttgaa | 1200 |
| acaggagtta tggatattcc atttggacca agtaaatata atgcaggtaa gatgatgcca | 1260 |
| gtaagggata tcttggatg cgttagatac ttagaatttg gaaatgttcc atttactgaa | 1320 |
| gaaataaaga attcaacag agaaagatta caagaaagag ccaaatttga aggtagagat | 1380 |
| gttagcttcc aaatggttat agatgacata tttgcagttg gaaaaggaag attaattgga | 1440 |
| agaccagaag gacaaggaca aggacaagga caaggacaag gagagaaaaa gactattgtt | 1500 |
| cttggagtta ttggttcaga ctgtcatgca gttggtaaca aaatattaga ccactcattt | 1560 |
| acaaatgcag gcttcaatgt tgttaacata ggagttttat catcacagga agatttttata | 1620 |
| aatgcagcta tagaaactaa agcagacctt atatgtgttt cttcattata tggacaggga | 1680 |
| gaaattgact gtaaaggatt aagagaaaag tgtgatgaag caggacttaa aggaataaaa | 1740 |
| ttatttgttg gcggaaacat tgttgttggt aaacaaaact ggccagatgt tgaacagaga | 1800 |
| tttaaagcaa tgggatttga tagagtatat ccaccaggaa catctccaga aacaacaata | 1860 |
| gctgatatga agaagttttt aggagtagaa taa | 1893 |

<210> SEQ ID NO 6
<211> LENGTH: 1599
<212> TYPE: DNA
<213> ORGANISM: Artificial sequence
<220> FEATURE:
<223> OTHER INFORMATION: Synthetic DNA

<400> SEQUENCE: 6

| | |
|---|---|
| atggggaatg tagattattc taaatattca aaacttagcc cattcgagtt agccgatagc | 60 |
| ctgattgctt tggcacagag taagcgggac cgcttaatgc tcaatgctgg acgaggaaac | 120 |
| cctaattttc tggctaccct gccacgtagg gcttttttc aattaggttt attttctgcc | 180 |
| acagaatcag aattttcatt ttcttacatg ccagaaggct taggtgggtt cccccgtcct | 240 |

```
gtcggtttgc aatcacgttt tgataatttt ctcatgcaga accgggataa acctggagtt    300
ttatttctgg gaaaagcagt gtcttatgtg agagaccaat tgggtttaga tccagatatg    360
tttctgcttg aaatggtcga agggattcta ggatgtaact accctgtacc tgatcgcatg    420
ctccgtgtca gtgaaacaat tattaaagag tatctgttac aggaaatggg cgtaaaaagt    480
atgcccaagg aaggcttgga cctgtttgcg gttgaaggcg aaccgcagc catggcttat     540 atatttaact ccttaaaaga aaacaagatt attaatactg acgaccgaat tgcaatcggc    600
agaccgattt ttacgccgta tctggaaatt cccaaactga atgactatca gcttgaagaa    660 attttattg aagctgatcc caatctgggc tggcaatatc ctgagtctga attaagaaag    720
ttagaagacc cttcaatcaa ggcattcttt ttagtcaatc cgagcaaccc gccttctgtc    780
aaaataagtg atgaaggatt gctaaatactg gcagatattg taagaaaacg tcctgacctg    840
attattttga cagatgatat ctatggaact tttgcagatg actttaagtc acttttttgca   900 atttgcccaa ataatactat tttagtttat tcattctcaa agtactttgg ggctacaggc    960
tggagacttg gcattattgc gctgtcgaat aacaatatca ttgatcagaa gattgcagcg   1020
ctttcagatc aggaaaagca ggaacttgaa gaacgttatt catcattaac tactgaacca   1080
gaaaaaatca gtttattga ccgtttggta gcagatagcc gtaatgttgc actgaatcac    1140
accgcaggtc tgtcaacacc gcagcaggta cagatggttc tttttgccct gtttaatatg   1200
atggattctc gtcaggctta taaaaagct gtcaagtctg tagtccggga acgcgatgct    1260
gcactttata gacagcttgg tgttgaagtc cctgaagatc ttaacgctgt tgactattac   1320
accttggtag atctggaaag aacagcccgc atattatatg gtgacgattt tgccaactgg   1380
gtcatggtca ataaaaaccc gacagaatta ttatttcggg tagcagatga aaccggtgtc   1440
gttctgttgc caggttctgg ctttggggta tcccatccat cggcacgtgc ttcattagcc   1500
aatctgaatg cttaccaata tgctgcaatc ggtgattctc tacgacgctt tgccgaagat   1560
gcctatcagg aatatctggg aactaaaaaa gatgagtcc                          1599
```

<210> SEQ ID NO 7
<211> LENGTH: 1599
<212> TYPE: DNA
<213> ORGANISM: Artificial sequence
<220> FEATURE:
<223> OTHER INFORMATION: Synthetic DNA

<400> SEQUENCE: 7

```
atggggaatg tagattattc taaatattca aaacttagcc cattcgagtt agccgatagc     60
ctgattgctt tggcacagag taagcgggac cgcttaatgc tcaatgctgg acgaggaaac   120
cctaattttc tggctaccct gccacgtagg gcttttttc aattaggttt attttctgcc    180
acagaatcag aatttcatt ttcttacatg ccagaaggct taggtgggtt ccccgtcct    240 gtcggtttgc aatcacgttt tgataatttt ctcatgcaga accgggataa acctggagtt    300
ttatttctgg gaaaagcagt gtcttatgtg agagaccaat tgggtttaga tccagatatg    360
tttctgcttg aaatggtcga agggattcta ggatgtaact accctgtacc tgatcgcatg    420
ctccgtgtca gtgaaacaat tattaaagag tatctgttac aggaaatggg cgtaaaaagt    480
atgcccaagg aaggcttgga cctgtttgcg gttgaaggcg aaccgcagc catggcttat     540 atatttaact ccttaaaaga aaacaagatt attaatactg acgaccgaat tgcaatcggc    600
agaccgattt ttacgccgta tctggaaatt cccaaactga atgactatca gcttgaagaa    660
```

| | |
|---|---|
| atttttattg aagctgatcc caatctgggc tggcaatatc ctgagtctga attaagaaag | 720 |
| ttagaagacc cttcaatcaa ggcattcttt ttagtcaatc cgagcaaccc gccttctgtc | 780 |
| aaaataagtg atgaaggatt gctaatactg gcagatattg taagaaaacg tcctgacctg | 840 |
| attattttga cagatgatct ctatggaact tttgcagatg actttaagtc acttttttgca | 900 |
| atttgcccaa ataatactat tttagtttat tcattctcaa agtactttgg ggctacaggc | 960 |
| tggagacttg gcattattgc gctgtcgaat aacaatatca ttgatcagaa gattgcagcg | 1020 |
| cttcagatc aggaaaagca ggaacttgaa gaacgttatt catcattaac tactgaacca | 1080 |
| gaaaaaatca agtttattga ccgtttggta gcagatagcc gtaatgttgc actgaatcac | 1140 |
| accgcaggtc tgtcaacacc gcagcaggta cagatggttc ttttttgccct gtttaatatg | 1200 |
| atggattctc gtcaggctta taaaaaagct gtcaagtctg tagtccggga acgcgatgct | 1260 |
| gcactttata gacagcttgg tgttgaagtc cctgaagatc ttaacgctgt tgactattac | 1320 |
| accttggtag atctggaaag aacagcccgc atattatatg gtgacgattt tgccaactgg | 1380 |
| gtcatggtca ataaaaaccc gacagaatta ttatttcggg tagcagatga aaccggtgtc | 1440 |
| gttctgttgc caggttctgg ctttgggta tcccatccat cggcacgtgc ttcattagcc | 1500 |
| aatctgaatg cttaccaata tgctgcaatc ggtgattctc tacgacgctt tgccgaagat | 1560 |
| gcctatcagg aatatctggg aactaaaaaa gatgagtcc | 1599 |

<210> SEQ ID NO 8
<211> LENGTH: 1599
<212> TYPE: DNA
<213> ORGANISM: Artificial sequence
<220> FEATURE:
<223> OTHER INFORMATION: Synthetic DNA

<400> SEQUENCE: 8

| | |
|---|---|
| atggggaatg tagattattc taaatattca aaacttagcc cattcgagtt atccgatagc | 60 |
| ctgattgctt tggcacagag taagcgggac cgcttaatgc tcaatgctgg acgaggaaac | 120 |
| cctaattttc tggctaccct gccacgtagg gcttttttc aattaggttt attttctgcc | 180 |
| acagaatcag aattttcatt ttcttacatg ccagaaggct taggtgggtt cccccgtcct | 240 |
| gtcggtttgc aatcacgttt tgataatttt ctcatgcaga accgggataa acctggagtt | 300 |
| ttatttctgg gaaaagcagt gtcttatgtg agagaccaat tgggtttaga tccagatatg | 360 |
| tttctgcttg aaatggtcga agggattcta ggatgtaact accctgtacc tgatcgcatg | 420 |
| ctccgtgtca gtgaaacaat tattaaagag tatctgttac aggaaatggg cgtaaaaagt | 480 |
| atgcccaagg aaggcttgga cctgtttgcg gttgaaggcg gaaccgcagc catggcttat | 540 |
| atatttaact ccttaaaaga aaacaagatt attaatactg acgaccgaat tgcaatcggc | 600 |
| agaccgattt tacgccgta tctggaaatt cccaaactga atgactatca gcttgaagaa | 660 |
| atttttattg aagctgatcc caatctgggc tggcaatatc ctgagtctga attaagaaag | 720 |
| ttagaagacc cttcaatcaa ggcattcttt ttagtcaatc cgagcaaccc gccttctgtc | 780 |
| aaaataagtg atgaaggatt gctaatactg gcagatattg taagaaaacg tcctgacctg | 840 |
| attattttga cagatgatat ctatggaact tttgcagatg actttaagtc acttttttgca | 900 |
| atttgcccaa ataatactat tttagtttat tcattctcaa agtactttgg ggctacaggc | 960 |
| tggagacttg gcattattgc gctgtcgaat aacaatatca ttgatcagaa gattgcagcg | 1020 |
| cttcagatc aggaaaagca ggaacttgaa gaacgttatt catcattaac tactgaacca | 1080 |
| gaaaaaatca agtttattga ccgtttggta gcagatagcc gtaatgttgc actgaatcac | 1140 |

```
accgcaggtc tgtcaacacc gcagcaggta cagatggttc tttttgccct gtttaatatg    1200
atggattctc gtcaggctta taaaaaagct gtcaagtctg tagtccggga acgcgatgct    1260
gcactttata gacagcttgg tgttgaagtc cctgaagatc ttaacgctgt tgactattac    1320
accttggtag atctggaaag aacagcccgc atattatatg gtgacgattt tgccaactgg    1380
gtcatggtca ataaaaaccc gacagaatta ttatttcggg tagcagatga aaccggtgtc    1440
gttctgttgc caggttctgg ctttggggta tcccatccat cggcacgtgc ttcattagcc    1500
aatctgaatg cttaccaata tgctgcaatc ggtgattctc tacgacgctt tgccgaagat    1560
gcctatcagg aatatctggg aactaaaaaa gatgagtcc                           1599
```

<210> SEQ ID NO 9
<211> LENGTH: 1599
<212> TYPE: DNA
<213> ORGANISM: Artificial sequence
<220> FEATURE:
<223> OTHER INFORMATION: Synthetic DNA

<400> SEQUENCE: 9

```
atggggaatg tagattattc taaatattca aaacttagcc cattcgagtt atccgatagc      60
ctgattgctt tggcacagag taagcgggac cgcttaatgc tcaatgctgg acgaggaaac     120
cctaattttc tggctaccct gccacgtagg gctttttttc aattaggttt attttctgcc     180
acagaatcag aattttcatt ttcttacatg ccagaaggct taggtgggtt cccccgtcct     240
gtcggtttgc aatcacgttt tgataatttt ctcatgcaga accgggataa acctggagtt     300
ttatttctgg gaaaagcagt gtcttatgtg agagaccaat gggtttaga tccagatatg      360 tttctgcttg aaatggtcga agggattcta ggatgtaact accctgtacc tgatcgcatg     420
ctccgtgtca gtgaaacaat tattaaagag tatctgttac aggaaatggg cgtaaaaagt     480
atgcccaagg aaggcttgga cctgtttgcg gttgaaggcg aaccgcagc catggcttat      540 atatttaact ccctaaaaga aaacaagatt attaatactg acgaccgaat tgcaatcggc     600
agaccgattt ttacgccgta tctggaaatt cccaaactga atgactatca gcttgaagaa    660 attttttattg aagctgatcc caatctgggc tggcaatatc ctgagtctga attaagaaag   720
ttagaagacc cttcaatcaa ggcattcttt ttagtcaatc cgagcaaccc gccttctgtc    780
aaaataagtg atgaaggatt gctaatactg gcagatattg taagaaaacg tcctgacctg    840
attattttga cagatgatct ctatggaact tttgcagatg actttaagtc acttttttgca   900 atttgcccaa ataatactat tttagtttat tcattctcaa agtactttgg ggctacaggc    960
tggagacttg gcattattgc gctgtcgaat aacaatatca ttgatcagaa gattgcagcg   1020
ctttcagatc aggaaaagca ggaacttgaa gaacgttatt catcattaac tactgaacca   1080
gaaaaaatca gtttattga ccgtttggta gcagatagcc gtaatgttgc actgaatcac    1140
accgcaggtc tgtcaacacc gcagcaggta cagatggttc tttttgccct gtttaatatg   1200
atggattctc gtcaggctta taaaaaagct gtcaagtctg tagtccggga acgcgatgct   1260
gcactttata gacagcttgg tgttgaagtc cctgaagatc ttaacgctgt tgactattac   1320
accttggtag atctggaaag aacagcccgc atattatatg gtgacgattt tgccaactgg   1380
gtcatggtca ataaaaaccc gacagaatta ttatttcggg tagcagatga aaccggtgtc   1440
```

```
gttctgttgc caggttctgg ctttggggta tcccatccat cggcacgtgc ttcattagcc    1500
aatctgaatg cttaccaata tgctgcaatc ggtgattctc tacgacgctt tgccgaagat    1560
gcctatcagg aatatctggg aactaaaaaa gatgagtcc                           1599
```

DOUBLE ENZYME TANDEM PREPARATION METHOD OF L-2-AMINOBUTYRIC ACID

TECHNICAL FIELD

The disclosure relates to a double enzyme tandem preparation method of L-2-aminobutyric acid, and belongs to the technical field of bioengineering.

BACKGROUND

L-2-aminobutyric acid (L-ABA), as a nonprotein amino acid, is an important pharmaceutical intermediate. For example, it can be used to synthesize antiepileptic drugs levetiracetam and brivaracetam, and anti-tuberculosis drugs ethambutol, etc. At present, the synthetic methods of L-2-aminobutyric acid mainly include chemical synthesis and biosynthesis. For chemical asymmetric synthesis of L-2-aminobutyric acid, it is required to use highly toxic chemical reagents such as cyanide and bromine as synthetic raw materials, and then use a chemical chiral resolving agent to achieve the resolution of racemic intermediates. The reaction process has the disadvantages such as highly toxic compounds, serious environmental pollution, low product chiral purity, and harsh reaction conditions such as high temperature and high pressure. Compared with chemical synthesis, biocatalytic synthesis of L-2-aminobutyric acid has incomparable advantages. There are mainly two types of biosynthesis. One is an enzymatic resolution method, specifically, racemic DL-2-aminobutyric acid is catalyzed by corresponding enzyme to produce L-2-aminobutyric acid, but the theoretical output is only 50%. The other is an enzyme synthesis method, specifically, the substrate is threonine, threonine produces 2-ketobutyric acid under the action of threonine dehydrogenase, and the 2-ketobutyric acid is reduced to L-2-aminobutyric acid under the action of transaminase or dehydrogenase. The enzyme synthesis method has the disadvantages of requiring a large number of amino donors, and high prices of cofactor regeneration systems and substrates, and is not suitable for industrial production.

SUMMARY

The disclosure provides a method for biosynthesizing L-2-aminobutyric acid, using L-glutamate as a substrate and a double enzyme tandem system to catalyze L-glutamate to produce L-2-aminobutyric acid. The two enzymes are L-glutamate mutase and L-aspartate-β-decarboxylase. In the double enzyme tandem system, the concentration of the substrate L-glutamate is 10-30 mmol/L. The L-glutamate mutase and the L-aspartate-β-decarboxylase are added to the double enzyme tandem system at a ratio of (4-6):1. The dosage of the L-aspartate-β-decarboxylase used is 0.5-5 mg/mL.

In one embodiment, in the double enzyme tandem system, the concentration of the substrate L-glutamate is 10-20 mmol/L, and the L-glutamate mutase and the L-aspartate-β-decarboxylase are added to the double enzyme tandem system at a mass ratio of (4-6):1.

In one embodiment, the dosage of the L-aspartate-β-decarboxylase used is 2-3 mg/mL.

In one embodiment, the double enzyme tandem system also contains 0.5-1.5 mmol/L dithiothreitol, 0.5-1 mmol/L pyridoxal phosphate, 0.01-0.02 mmol/L adenosylcobalamin, 0.02-0.2 mmol/L pyruvic acid and 18-22 mM $K_2HPO_4$/$KH_2PO_4$ buffer at a pH of 6.5-7.5.

In one embodiment, the temperature of a catalytic reaction is 35-39° C., and the reaction time is 10-30 h.

In one embodiment, the nucleotide sequence of a gene encoding the L-glutamate mutase is set forth in SEQ ID NO:5.

In one embodiment, the amino acid sequence of the L-aspartate-β-decarboxylase is set forth in SEQ ID NO:1 or SEQ ID NO:2 or SEQ ID NO:3 or SEQ ID NO:4; the L-aspartate-β-decarboxylase includes K18A/V287I, K18A/V287L, K18S/V287I and K18S/V287L. The amino acid sequence of K18A/V287I is set forth in SEQ ID NO:1, and the nucleotide sequence encoding K18A/V287I is set forth in SEQ ID NO:6; the amino acid sequence of K18A/V287L is set forth in SEQ ID NO:2, and the nucleotide sequence encoding K18A/V287L is set forth in SEQ ID NO:7; the amino acid sequence of K18S/V287I is set forth in SEQ ID NO:3, and the nucleotide sequence encoding K18S/V287I is set forth in SEQ ID NO:8; and the amino acid sequence of K18S/V287L is set forth in SEQ ID NO:4, and the nucleotide sequence encoding K18S/V287L is set forth in SEQ ID NO:9.

In one embodiment, a preparation method of the L-glutamate mutase includes: ligating the gene encoding L-glutamate mutase and having the nucleotide sequence set forth in SEQ ID NO:5 to a plasmid pET-28a to obtain a recombinant plasmid pET-28a-GlmES, transforming the recombinant plasmid into *Escherichia coli* BL21 to obtain recombinant *Escherichia coli* BL21/pET-28a-GlmES, and fermenting the recombinant *Escherichia coli* BL21/pET-28a-GlmES to produce L-glutamate mutase.

In one embodiment, the fermentation is culturing *Escherichia coli* in an environment containing IPTG, and induce culturing at 28-32° C. for 15-30 h.

In one embodiment, the production is adding IPTG to the strain culture of the recombinant *Escherichia coli* BL21/pET-28a-GlmES with an $OD_{600}$ of 0.6-0.8, and induce culturing at 28-32° C. for 15-30 h to obtain bacterial cells.

In one embodiment, the preparation method of the L-aspartate-β-decarboxylase includes: ligating the gene encoding the L-aspartate-β-decarboxylase and having the nucleotide sequence set forth in SEQ ID NO:6 or SEQ ID NO:7 or SEQ ID NO:8 or SEQ ID NO:9 to the plasmid pET-28a to obtain the recombinant plasmid pET-28a-K18A/V287I or pET-28a-K18A/V287L or pET-28a-K18S/V287I or pET-28a-K18S/V287L; transforming the recombinant plasmid into *Escherichia coli* BL21 to obtain recombinant *Escherichia coli* BL21/pET-28a-K18A/V287I or BL21/pET-28a-K18A/V287L or BL21/pET-28a-K18S/V287I or BL21/pET-28a-K18S/V287L; and producing the L-aspartate-β-decarboxylase by the recombinant strain.

In one embodiment, the fermentation is culturing *Escherichia coli* in an environment containing IPTG, and induce culturing at 28-32° C. for 15-30 h.

In one embodiment, the production process is adding IPTG to the strain culture of the recombinant *Escherichia coli* BL21/pET-28a-K18A/V287I or BL21/pET-28a-K18A/V287L or BL21/pET-28a-K18S/V287I or BL21/pET-28a-K18S/V287L with an $OD_{600}$ of 0.6-0.8, and induce culturing at 28-32° C. for 15-30 h to obtain bacterial cells.

In one embodiment, the preparation method of the L-glutamate mutase and the L-aspartate-β-decarboxylase further includes: collecting and breaking the cultured bacterial cells, and separating and purifying a target enzyme protein to obtain an electrophoretically pure enzyme.

The beneficial effects of the disclosure: The disclosure realizes for the first time that L-glutamate is used as a substrate to be converted into L-2-aminobutyric acid through a double enzyme tandem system. When the dosage of the L-aspartate-β-decarboxylase used is 2 mg/mL, and the reaction time is 24 h, 8.5 mmol/L L-2-aminobutyric acid is produced by the conversion with a molar conversion rate of 85.00%. The disclosure adopts the substrate with low price and a simple process, and can reduce the production cost of L-2-aminobutyric acid.

DETAILED DESCRIPTION

Figure 1:
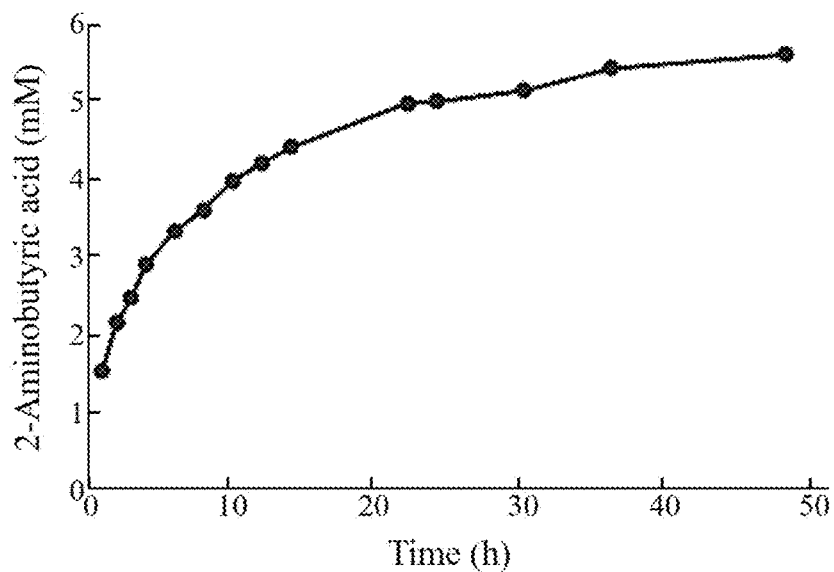
FIG. 1 shows a reaction process of synthesis of L-2-aminobutyric acid from L-glutamate catalyzed by L-glutamate mutase and L-aspartate-β-decarboxylase.
Figure 2:
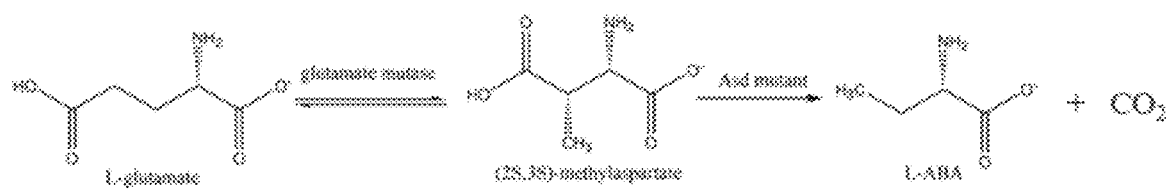
FIG. 2 shows a schematic diagram of a double enzyme tandem reaction.

LB culture medium: Peptone 10 g/L, yeast extract 5 g/L, and NaCl 10 g/L.

2YT culture medium: Peptone 16 g/L, yeast extract 10 g/L, and NaCl 5 g/L.

Determination of the content of L-2-aminobutyric acid: A reaction solution is derivatized with phenyl-isothiocyanate (PITC). The specific steps are as follows: add 250 μL of a 0.1 mol/L PITC acetonitrile solution and 250 μL of a 1 mol/L triethylamine acetonitrile solution to 500 μL of sample, mix the solution well, place the solution at room temperature in dark for 1 h, and add 500 μL of a n-hexane solution; and oscillate the solution on a vortex oscillator for 1 min, allow the solution to stand for 60 min, suck the lower layer solution, and filter the lower layer solution with a 0.45 μm organic filter membrane. The derivative product is determined by HPLC: the chromatographic column is La Chrom C18 (5 μm, 4.6×250 mm); the mobile phase A solution is an 80% (V/V) acetonitrile aqueous solution, and the B solution is a 97:3 (V/V, pH 6.5) 0.1 mol/L sodium acetate-acetonitrile solution. Gradient elution is adopted: in 0-20 min, the B solution is decreased from 95% to 65%; in 20-30 min, the B solution is increased from 65% to 95%; in 30-35 min, the gradient of the B solution is not changed. The detection wavelength is 254 nm, and the column temperature is 40° C.

Determination method of the enzyme activity of L-aspartate-β-decarboxylase: A reaction system includes 10 mM $K_2HPO_4/KH_2PO_4$ buffer at a pH of 6.6, 0.05 mg/mL L-aspartate-β-decarboxylase, 50 mmol/L DL-3-methylaspartate, 0.5 mmol/L pyridoxal phosphate, and 0.05 mmol/L pyruvic acid. The reaction volume is 1 mL. After reacting at 37° C. for 2 min, inactivate the reaction system at 100° C. for 10 min. After centrifuging at 12000 rpm for 2 min, take the supernatant to detect the yield of L-2-aminobutyric acid. The enzyme activity is defined as that the amount of enzyme required to produce 1 μM L-2-aminobutyric acid per minute is an activity unit.

Determination method of the enzyme activity of L-glutamate mutase: A reaction system includes 10 mM $K_2HPO_4/KH_2PO_4$ buffer at a pH of 6.6, 0.1 mg/mL L-glutamate mutase, 100 mmol/L L-glutamate, 0.01 mmol/L adenosylcobalamin, 1 mmol/L dithiothreitol, 10 mmol/L KCl, 1 mmol/L $MgCl_2$, and 0.16 mg/mL 3-methylaspartate lyase. The reaction volume is 1 mL. After reacting at 37° C. for 1 min, inactivate the reaction system at 100° C. for 10 min. After centrifuging at 12000 rpm for 2 min, measure the supernatant at $OD_{240}$. The enzyme activity is defined as that the amount of enzyme required to produce 1 μM 3-methylaspartic acid per minute is an activity unit.

Example 1 Construction of Recombinant *Escherichia coli* BL21/pET-28-GlmES

A gene encoding fusion L-glutamate mutase was ligated by a glmE subunit from *Clostridium tetanomorphum* and a mutS subunit from *Clostridium cochlearium* through a (glycine-glutamine) repeating decapeptide. The nucleotide sequence of the gene was set forth in SEQ ID NO:5. The gene was synthesized by Suzhou Genewiz Company and ligated to a plasmid pET-28a. The recombinant plasmid pET-28a-glmES was transformed into *Escherichia coli* BL21 competent cells to obtain recombinant *Escherichia coli* BL21/pET-28a-glmES.

Example 2 Construction of Recombinant *Escherichia coli* Expressing L-Aspartate-β-Decarboxylase The gene encoding the L-aspartate-β-decarboxylase mutant and having a nucleotide sequence set forth in SEQ ID NO:6, SEQ ID NO:7, SEQ ID NO:8 or SEQ ID NO:9 was respectively ligated to a plasmid pET-28a to obtain recombinant plasmids pET-28a-K18A/V287I, pET-28a-K18A/V287L, pET-28a-K18S/V287I and pET-28a-K18S/V287L. The above recombinant plasmids pET-28a-K18A/V287I, pET-28a-K18A/V287L, pET-28a-K18S/V287I and pET-28a-K18S/V287L were respectively transferred into *Escherichia coli* BL21 competent cells, and recombinant *Escherichia coli* BL21/pET-28a-K18A/V287I, BL21/pET-28a-K18A/V287L, BL21/pET-28a-K18S/V287I and BL21/pET-28a-K18S/V287L were obtained by screening.

Example 3 Expression of L-Glutamate Mutase

The recombinant *Escherichia coli* BL21/pET-28a-glmES prepared in Example 1 was inoculated into 5 mL of an LB medium with a kanamycin concentration of 50 μg/mL, and cultured overnight at 37° C. and 200 rpm under shaking. The above overnight culture was inoculated into a 2YT medium containing kanamycin with a concentration of 50 μg/mL at an inoculum amount of 1% (V/V), and cultured under shaking at 37° C. and 200 rpm until the $OD_{600}$ of the bacterial solution was 0.6-0.8. IPTG was added to a final concentration of 0.2 mmol/L, and culture was induced at 30° C. for about 20 h to obtain bacterial cells. Bacterial cells were collected by centrifugation at 6000 rpm and ultrasonically broken, and protein was purified using a His Trap HP affinity column. The target protein was detected by SDS-PAGE.

Example 4 Expression of L-Aspartate-β-Decarboxylase

The recombinant *Escherichia coli* BL21/pET-28a-K18A/V287I, BL21/pET-28a-K18A/V287L, BL21/pET-28a-K18S/V287I and BL21/pET-28a-K18S/V287L prepared in Example 2 were respectively inoculated into 5 mL of an LB medium with a kanamycin concentration of 50 μg/mL, and cultured overnight under shaking at 37° C. and 200 rpm. The above overnight culture was inoculated into a 2YT medium containing kanamycin with a concentration of 50 μg/mL at an inoculum amount of 1%, and cultured under shaking at 37° C. and 200 rpm until the $OD_{600}$ of the bacterial solution was 0.6-0.8. IPTG was added to a final concentration of 0.2 mmol/L, and culture was induced at 30° C. for about 20 h to obtain bacterial cells. Bacterial cells were collected by centrifugation at 6000 rpm and ultrasonically broken, and protein was purified using a His Trap HP affinity column. The target protein was detected by SDS-PAGE.

Example 5 Double Enzyme Tandem Preparation of L-2-Aminobutyric Acid

In the double enzyme tandem system, the concentration of the substrate L-glutamate was 10 mmol/L. L-glutamate mutase and L-aspartate-β-decarboxylase were added to 1 mL of reaction system at a ratio of 4:1 according to the ratio of enzyme activity units, so that the dosage of the L-aspartate-β-decarboxylase in the reaction system was 1 mg/mL, the enzyme activity of the L-aspartate-β-decarboxylase was 7 U/mL, and the activity of the glutamate mutase was 28 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. The reaction was performed at 37° C. for 24 h. Samples were taken every 1-2 h, and L-2 aminobutyric acid in the reaction solution was detected by HPLC. The result is shown in FIG. 1. 5.6 mmol/L L-2 aminobutyric acid is produced by the conversion with a molar conversion rate of 56.00%. When the dosage of the L-aspartate-β-decarboxylase is 2 mg/mL, after 24 h of reaction, 8.5 mmol/L L-2 aminobutyric acid is produced by the conversion with a molar conversion rate of 85.00%.

Example 6 Double Enzyme Tandem Preparation of L-2-Aminobutyric Acid

In the double enzyme tandem system, the concentration of the substrate L-glutamate was 10 mmol/L. L-glutamate mutase and L-aspartate-β-decarboxylase were added to 1 mL of reaction system at a ratio of 6:1 according to the ratio of enzyme activity units, so that the dosage of the L-aspartate-β-decarboxylase in the reaction system was 1 mg/mL, the enzyme activity of the L-aspartate-β-decarboxylase was 7 U/mL, and the activity of the glutamate mutase was 42 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. The reaction was performed at 37° C. for 24 h. Samples were taken every 1-2 h, and L-2 aminobutyric acid in the reaction solution was detected by HPLC. The result shows that 5.9 mmol/L L-2 aminobutyric acid is produced by the conversion with a molar conversion rate of 59.00%. When the dosage of the L-aspartate-β-decarboxylase is 2 mg/mL, after 24 h of reaction, 8.8 mmol/L L-2 aminobutyric acid is produced by the conversion with a molar conversion rate of 88.00%.

Comparative Example 1

In the double enzyme tandem system, the concentration of the substrate L-glutamate was 10 mmol/L. L-glutamate mutase and wild type L-aspartate-β-decarboxylase were added to 1 mL of reaction system at a ratio of 4:1 according to the ratio of enzyme activity units, so that the dosage of the L-aspartate-β-decarboxylase in the reaction system was 1 mg/mL, the enzyme activity of the L-aspartate-β-decarboxylase was 0 U/mL, and the activity of the glutamate mutase was 28 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. The reaction was performed at 37° C. for 24 h. Samples were taken every 1-2 h, and L-2 aminobutyric acid in the reaction solution was detected by HPLC. The result shows that 0 mmol/L L-2 aminobutyric acid is produced by the conversion with a molar conversion rate of 0%. When the dosage of the L-aspartate-β-decarboxylase is 2 mg/mL, after 24 h of reaction, 0 mmol/L L-2 aminobutyric acid is produced by the conversion with a molar conversion rate of 0%.

Comparative Example 2

In the double enzyme tandem system, the concentration of the substrate L-glutamate was 10 mmol/L. L-glutamate mutase and L-aspartate-β-decarboxylase were added to 1 mL of reaction system at a ratio of 1:1 according to the ratio of enzyme activity units, so that the dosage of the L-aspartate-β-decarboxylase in the reaction system was 1 mg/mL, the enzyme activity of the L-aspartate-β-decarboxylase was 7 U/mL, and the activity of the glutamate mutase was 7 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. After 24 h of reaction at 37° C., 2.8 mmol/L L-2 aminobutyric acid is produced by the conversion with a molar conversion rate of 28.00%.

Comparative Example 3

In the double enzyme tandem system, the concentration of the substrate L-glutamate was 10 mmol/L. L-glutamate mutase and L-aspartate-β-decarboxylase were added to 1 mL of reaction system at a ratio of 2:1 according to the ratio of enzyme activity units, so that the dosage of the L-aspartate-β-decarboxylase in the reaction system was 1 mg/mL, the enzyme activity of the L-aspartate-β-decarboxylase was 7 U/mL, and the activity of the glutamate mutase was 14 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. After 24 h of reaction at 37° C., 4.5 mmol/L L-2 aminobutyric acid is produced by the conversion with a molar conversion rate of 45.00%.

Comparative Example 4

In the double enzyme tandem system, the concentration of the substrate L-glutamate was 10 mmol/L. L-glutamate mutase and L-aspartate-β-decarboxylase were added to 1 mL of reaction system at a ratio of 8:1 according to the ratio of enzyme activity units, so that the dosage of the L-aspartate-β-decarboxylase in the reaction system was 1 mg/mL, the enzyme activity of the L-aspartate-β-decarboxylase was 7 U/mL, and the activity of the glutamate mutase was 56 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer with a pH of 6.6. After 24 h of reaction at 37° C., 8.9 mmol/L L-2 aminobutyric acid is produced by the conversion with a molar conversion rate of 89.00%.

Comparative Example 5

In the double enzyme tandem system, the concentration of the substrate L-glutamate was 10 mmol/L. L-glutamate mutase and L-aspartate-β-decarboxylase were added to 1 mL of reaction system at a ratio of 1:2 according to the ratio of enzyme activity units, so that the dosage of the L-aspartate-β-decarboxylase in the reaction system was 2 mg/mL, the enzyme activity of the L-aspartate-β-decarboxylase was 14 U/mL, and the activity of the glutamate mutase was 7 U/mL. The reaction system also contained 1 mmol/L dithiothreitol, 0.5 mmol/L pyridoxal phosphate, 0.02 mmol/L adenosylcobalamin, 0.05 mmol/L pyruvic acid and 10 mM $K_2HPO_4/KH_2PO_4$ buffer at a pH of 6.6. After 24 h of reaction at 37° C., 4.6 mmol/L L-2 aminobutyric acid is produced by the conversion with a molar conversion rate of 46.00%.

---

What is claimed is:

1. A method for biosynthesizing L-2-aminobutyric acid, comprising using L-glutamate as a substrate and a double enzyme tandem reaction system to catalyze L-glutamate to produce L-2-aminobutyric acid, wherein the two enzymes in the double enzyme tandem reaction system are L-glutamate mutase and L-aspartate-B-decarboxylase, wherein the amino acid sequence of the L-aspartate-B-decarboxylase is set forth in SEQ ID NO:1 or SEQ ID NO:2 or SEQ ID NO:3 or SEQ ID NO:4; in the double enzyme tandem reaction system, a concentration of the substrate L-glutamate is 10-30 mmol/L; the L-glutamate mutase and the L-aspartate-B-decarboxylase are added to the double enzyme tandem reaction system at a ratio of (4-6):1; and a dosage of the L-aspartate-B-decarboxylase is 0.5-5 mg/mL.

2. The method of claim 1, wherein in the double enzyme tandem reaction system, the concentration of the substrate L-glutamate is 10-20 mmol/L, and the L-glutamate mutase and the L-aspartate-β-decarboxylase are added to the double enzyme tandem reaction system at a ratio of (4-6):1.

3. The method of claim 1, wherein the dosage of the L-aspartate-β-decarboxylase is 2-3 mg/mL.

4. The method of claim 1, wherein the double enzyme tandem reaction system also contains 0.5-1.5 mmol/L dithiothreitol, 0.5-1 mmol/L pyridoxal phosphate, 0.01-0.02 mmol/L adenosylcobalamin, 0.02-0.2 mmol/L pyruvic acid and 18-22 mM $K_2HPO_4/KH_2PO_4$ buffer at a pH of 6.5-7.5.

5. The method of claim 1, wherein a temperature of a catalytic reaction is 35-39° C., and the reaction time is 10-30 h.

6. The method of claim 1, wherein the nucleotide sequence of the gene encoding the L-glutamate mutase is set forth in SEQ ID NO:5.

7. The method of claim 1, wherein a preparation method of the L-glutamate mutase comprises: ligating the gene encoding L-glutamate mutase and having the nucleotide sequence set forth in SEQ ID NO:5 to a plasmid pET-28a to obtain a recombinant plasmid pET-28a-GlmES, transforming the recombinant plasmid into *Escherichia coli* BL21 to obtain recombinant *Escherichia coli* BL21/pET-28a-GlmES, and fermenting the recombinant *Escherichia coli* BL21/pET-28a-GlmES to produce the L-glutamate mutase.

8. The method of claim 7, wherein the fermentation is culturing the *Escherichia coli* in an environment containing IPTG, and induce culturing at 28-32° C. for 15-30 h.

9. The method of claim 8, wherein the L-glutamate mutase is prepared by: collecting and breaking the cultured bacterial cells, and separating and purifying a target enzyme protein to obtain an electrophoretically pure enzyme.

10. The method of claim 1, wherein the L-aspartate-β-decarboxylase is prepared by: ligating the gene encoding the L-aspartate-β-decarboxylase and having the nucleotide sequence as set forth in any of SEQ ID NO:6 to SEQ ID NO:9 to the plasmid pET-28a to obtain a recombinant plasmid, transforming the recombinant plasmid into *Escherichia coli* BL21 to obtain recombinant *Escherichia coli*, and fermenting the recombinant *Escherichia coli* to produce the L-aspartate-β-decarboxylase.

11. The method of claim 9, wherein the fermentation is culturing the *Escherichia coli* in an environment containing IPTG, and induce culturing at 28-32° C. for 15-30 h.

12. The method of claim 11, wherein the preparation method of the L-aspartate-β-decarboxylase further comprises: collecting and breaking the cultured bacterial cells, and separating and purifying a target enzyme protein to obtain an electrophoretically pure enzyme.

* * * * *